United States Patent
Hammill, Sr. et al.

(10) Patent No.: US 12,245,794 B1
(45) Date of Patent: Mar. 11, 2025

(54) SPINAL FIXATION SYSTEM HAVING A LOW PROFILE LOCKABLE CONNECTOR

(71) Applicant: Complex Spinal, LLC, Palm Beach Gardens, FL (US)

(72) Inventors: John E. Hammill, Sr., Palm Beach Gardens, FL (US); Greg Lentner, Palm Beach Gardens, FL (US)

(73) Assignee: Complex Spinal, LLC, Palm Beach Gardens, FL (US)

( * ) Notice: Subject to any disclaimer, the term of this patent is extended or adjusted under 35 U.S.C. 154(b) by 0 days.

(21) Appl. No.: 18/663,812

(22) Filed: May 14, 2024

(51) Int. Cl.
*A61B 17/70* (2006.01)
*A61B 17/56* (2006.01)

(52) U.S. Cl.
CPC ...... *A61B 17/7005* (2013.01); *A61B 17/7035* (2013.01); *A61B 17/705* (2013.01); *A61B 2017/564* (2013.01)

(58) Field of Classification Search
None
See application file for complete search history.

(56) References Cited

U.S. PATENT DOCUMENTS

| | | |
|---|---|---|
| 255,428 A | 3/1882 | Graham |
| 590,204 A | 9/1897 | Archer |
| 4,378,187 A | 3/1983 | Fullerton |
| 4,419,026 A | 12/1983 | Leto |
| 4,836,196 A | 6/1989 | Park et al. |
| 4,854,304 A | 8/1989 | Zielke |
| 4,887,595 A | 12/1989 | Heinig et al. |
| 4,887,596 A | 12/1989 | Sherman |
| 4,946,458 A | 8/1990 | Harms et al. |
| 4,950,269 A | 8/1990 | Gaines, Jr. |
| 5,002,542 A | 3/1991 | Frigg |
| 5,110,244 A | 5/1992 | Garman |
| 5,129,900 A | 7/1992 | Asher et al. |
| 5,133,717 A | 7/1992 | Chopin |
| 5,324,150 A | 6/1994 | Fullerton |
| 5,427,488 A | 6/1995 | Fullerton et al. |
| 5,443,467 A | 8/1995 | Biedermann et al. |
| 5,487,744 A | 1/1996 | Howland |
| 5,549,608 A | 8/1996 | Errico et al. |
| 5,569,247 A | 10/1996 | Morrison |

(Continued)

FOREIGN PATENT DOCUMENTS

| | | |
|---|---|---|
| EP | 0836835 A2 | 4/1998 |
| EP | 0836835 A3 | 4/1998 |

(Continued)

OTHER PUBLICATIONS

Anonymous, "Versalok Low Back Fixation System—Instrumentation Manual", Wright Medical Technology, Inc.—Arlington, TN, pp. 1-10, (1997).

(Continued)

*Primary Examiner* — Tessa M Matthews
(74) *Attorney, Agent, or Firm* — McHale & Slavin, P.A.

(57) ABSTRACT

A low profile spinal fixation system for use in securing a spinal rod to a vertebra using a lockable bone screw connector. The connector is configured to be removably connected to the head of a bone screw, and a spinal rod can then be used to physically connect a first vertebra to a second vertebra. The spinal rod is locked to the bone screw by use of a compressible upper collet.

10 Claims, 6 Drawing Sheets

(56) References Cited

U.S. PATENT DOCUMENTS

| | | |
|---|---|---|
| 5,584,834 A | 12/1996 | Errico et al. |
| 5,591,166 A | 1/1997 | Bernhardt et al. |
| 5,613,816 A | 3/1997 | Cabahug |
| 5,628,740 A | 5/1997 | Mullane |
| 5,669,911 A | 9/1997 | Errico et al. |
| 5,683,392 A | 11/1997 | Richelsoph et al. |
| 5,716,357 A | 2/1998 | Rogozinski |
| 5,733,285 A | 3/1998 | Errico et al. |
| 5,749,690 A | 5/1998 | Kutz |
| 5,788,443 A | 8/1998 | Cabahug |
| 5,800,435 A | 9/1998 | Errico et al. |
| 5,863,293 A | 1/1999 | Richelsoph |
| 5,947,966 A | 9/1999 | Drewry et al. |
| 5,964,760 A | 10/1999 | Richelsoph |
| 5,997,539 A | 12/1999 | Errico et al. |
| 6,010,503 A | 1/2000 | Richelsoph |
| 6,050,997 A | 4/2000 | Mullane |
| 6,063,090 A | 5/2000 | Schlapfer |
| 6,090,111 A | 7/2000 | Nichols |
| 6,102,952 A | 8/2000 | Koshino |
| 6,113,600 A | 9/2000 | Drummond et al. |
| 6,132,432 A | 10/2000 | Richelsoph |
| 6,162,234 A | 12/2000 | Freedland et al. |
| 6,187,005 B1 | 2/2001 | Brace et al. |
| RE37,227 E | 6/2001 | Brodbeck |
| 6,254,602 B1 | 7/2001 | Justis |
| 6,273,888 B1 | 8/2001 | Justis |
| 6,355,040 B1 | 3/2002 | Richelsoph et al. |
| RE37,665 E | 4/2002 | Ralph et al. |
| 6,413,258 B1 | 7/2002 | Bernhardt, Jr. |
| 6,416,515 B1 | 7/2002 | Wagner |
| 6,454,773 B1 | 9/2002 | Sherman et al. |
| 6,478,798 B1 | 11/2002 | Howland |
| 6,565,565 B1 | 5/2003 | Yuan et al. |
| 6,595,992 B1 | 7/2003 | Wagner et al. |
| 6,602,255 B1 | 8/2003 | Campbell et al. |
| 6,610,062 B2 | 8/2003 | Bailey et al. |
| 6,610,063 B2 | 8/2003 | Kumar et al. |
| 6,623,485 B2 | 9/2003 | Doubler et al. |
| 6,626,906 B1 | 9/2003 | Young |
| 7,105,029 B2 | 9/2006 | Doubler et al. |
| 7,335,201 B2 | 2/2008 | Doubler et al. |
| 7,658,582 B2 | 2/2010 | Doubler et al. |
| 7,744,633 B2 | 6/2010 | Berrevoets et al. |
| RE42,867 E | 10/2011 | Hammill, Sr. et al. |
| 9,649,135 B2 | 5/2017 | Doubler et al. |
| 10,136,925 B2 | 11/2018 | Shoshtaev |
| 10,751,090 B2 | 8/2020 | Biedermann et al. |
| 2002/0114680 A1 | 8/2002 | Stoewer et al. |
| 2003/0149487 A1 | 8/2003 | Doubler et al. |
| 2005/0053423 A1 | 3/2005 | Doubler et al. |
| 2007/0286703 A1 | 12/2007 | Doubler et al. |
| 2011/0190822 A1* | 8/2011 | Spitler .................. A61B 17/70 606/264 |
| 2015/0032162 A1* | 1/2015 | Biedermann ...... A61B 17/7035 606/278 |
| 2015/0173816 A1* | 6/2015 | Biedermann ...... A61B 17/8605 606/308 |
| 2016/0262816 A1* | 9/2016 | Doubler ............. A61B 17/8605 |
| 2019/0209214 A1* | 7/2019 | Biedermann ........ A61B 17/708 |

FOREIGN PATENT DOCUMENTS

| | | |
|---|---|---|
| EP | 0947174 A3 | 10/1999 |
| EP | 0947174 B1 | 10/1999 |

OTHER PUBLICATIONS

Anonymous, ", Strong, Simple and Low Profile—Ovation Polyaxial System", Osteotech, Inc. Spinal Systems.—Eatontown, NJ, pp. 1-6, (1999).

* cited by examiner

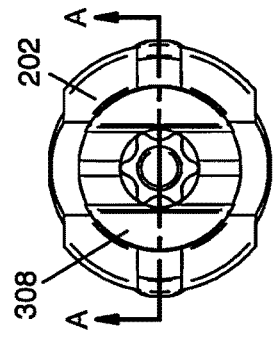
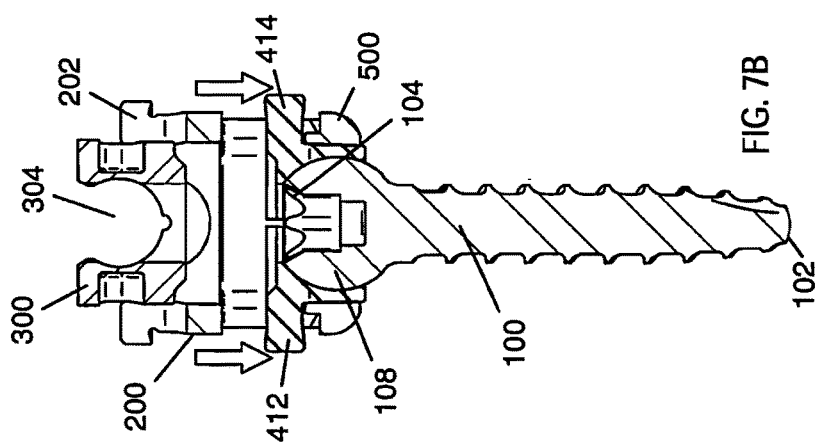
FIG. 6A
FIG. 6B
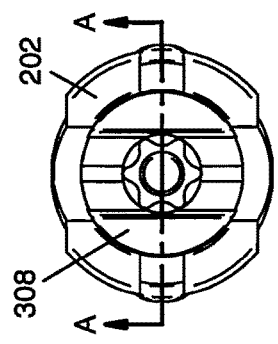
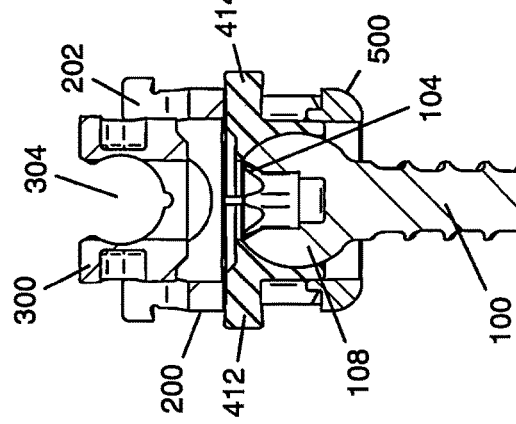
FIG. 7A
FIG. 7B

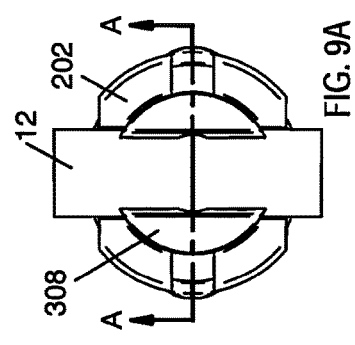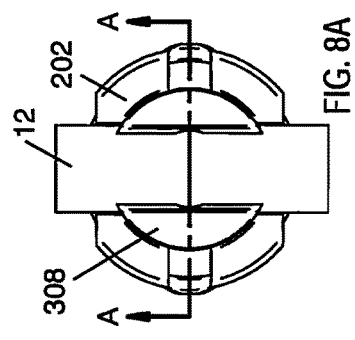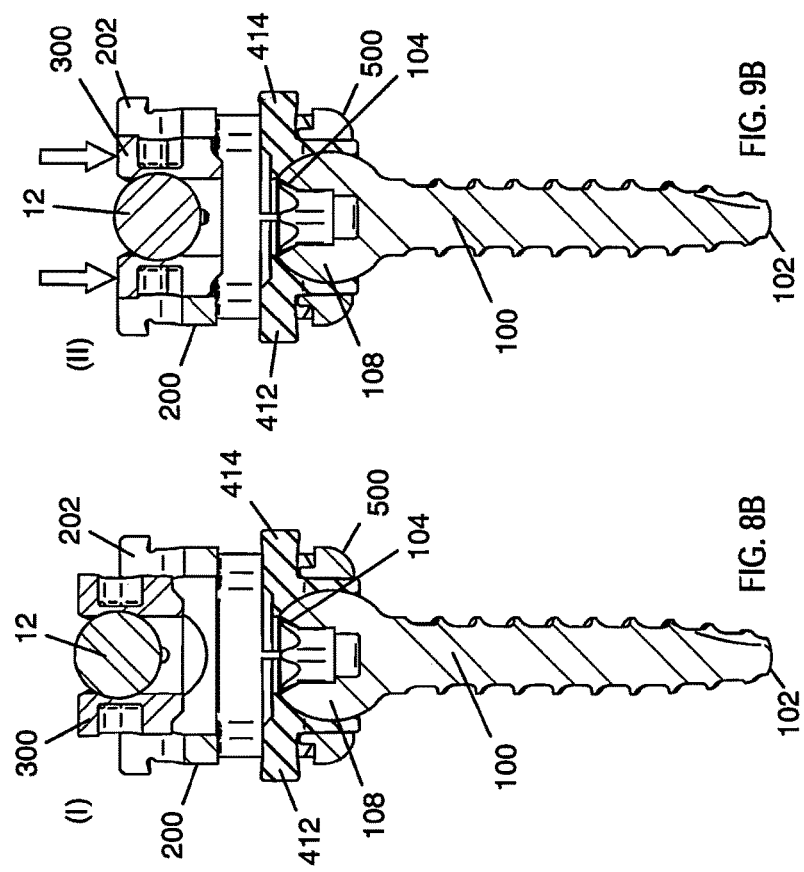

SPINAL FIXATION SYSTEM HAVING A LOW PROFILE LOCKABLE CONNECTOR

FIELD OF THE INVENTION

The instant invention relates to field of orthopedic surgery, namely a spinal fixation system for use in securing a spinal rod to a vertebra using a lockable bone screw connector.

BACKGROUND OF THE INVENTION

Spinal rod systems for use in facilitating spinal fusion, and for correcting and stabilizing spinal curvatures to correct spinal disorders or degenerative conditions, are well known in the art. Spinal rod systems include two or more bone screws with connector members coupled together with spinal rods. The conventional bone screw has a proximal end constructed and arranged to secure to a vertebrae, and a connector coupled to the distal end of the bone screw for receipt of a spinal rod. During a spinal correction procedure, a plurality of bone screws with connector members are fixed to vertebrae at various points on each side of the spinal midline. Thereafter, each of the connector members are on each side of the spinal midline and linked with the other fixation members by an elongated spinal rod, such that the spinal rod extends vertically along at least a portion of the length of the spine.

It is common practice to place bone screws into the vertebral bodies and then connect a metal rod between the bone screws to create a rigid structure between adjacent vertebral bodies. The spinal rod connector members are used for transversely and rigidly connecting adjacent spinal members together. By providing a rigid transverse connection between adjacent spinal rods, a stiffer construct can be created to enhance the promotion of spinal fusion.

Spinal rods are mounted by a surgeon in a custom-fit manner, both in length and angular positioning. Bending of the rod is common so that the rod is holding the vertebral portions in proper relation. There is not a predetermined distance between two spinal rods, and the rods may converge or diverge from each other. One spinal rod may have a portion directed at an angle different from that of a second other rod.

For these reasons there remains a need for a device which, in one simple action such as squeezing a lever, can reduce a posteriorly introduced rod into a pedicle screw and securely lock the connector to the pedicle screw to allow placement of the rod. Conversely, there remains a need for a similar device which, through an equally simple action, can unlock the connector from a pedicle screw thereby releasing the connector and adjoining rod from a set position.

Known prior art includes: U.S. Pat. No. 5,947,966 discloses a transverse connector system for linking adjacent spinal rods together. The system includes first and second connector portions which are slidably adjustable in relation to each other. Each connector portion includes an engaging member configured to receive a spinal rod. A wedge member is provided in each engaging member to secure each connector portion to the spinal rod. The wedge member includes a screw for engaging and biasing the spinal rod into a receptacle defined by the engaging member.

U.S. Pat. No. 5,683,392 discloses a multi planar locking mechanism for securing a spinal rod to the spinal column. The locking mechanism includes a bone fixation member for attachment to the bone member, the bone fixation member having a spherical portion; an inner housing member having a channel for receiving the rod and having a spherical portion for engaging the spherical portion of the bone fixation member; and an outer housing member for locking the inner housing member to the rod and the spherical portion of the bone fixation member.

U.S. Pat. No. 6,413,258 discloses a rod-to-rod coupler which includes a body having first and second coupler portions. Each coupler portion defines a concavity configured to receive a portion of an elongated spinal rod. A screw and nut assembly, which includes a screw and a flanged nut, is positioned adjacent each concavity. Each flanged nut has a flange portion which extends at least partially over one concavity.

U.S. Pat. No. 6,113,600 discloses a spinal fixation system having a pair of longitudinal members positionable adjacent the spine, an engaging member for engaging longitudinal members to the spine, a pair of wedge members each having a bearing surface configured to bear on a longitudinal member, and a connector configured to span a distance between the longitudinal members. The connector includes a pair of engaging members each having a fixation surface and a connecting surface, and a bridge member attached to the connecting surfaces.

U.S. Pat. No. 7,744,633 discloses a crosslink member for securing spinal rods having connector ends that include a brace and a locking member, each connector include an arcuate face resting on and securing a spinal rod. The locking member is a cam member that rotates relative to the locking member and engages the connector to displace the cam member. The crosslink includes a male connector with a cylindrical cross rod received by a cavity in a female connector. The cross rod is secured by a pivotable clamp device in the female connector, and the cross rod connector and female connector may pivot, rotate, and telescope relative to each other.

U.S. Pat. No. 10,136,925 discloses a spinal cross-connector having an elongated member, a first connector, and a second connector. The first connector and the second connector are configured to receive spinal rods and adaptable to directly attach with pedicle screws. The first connector includes a first collet head, a first clamp and a first locking means. The second connector includes a second collet head, a second clamp and a second locking means. The first locking means is configured to tighten over a first collet head and engage with the first connector. Similarly, the second locking means is configured to tighten over a second collet head and engage with the second connector. The engagement of the first locking means with the first connector and the second locking means with the second connector locks the spinal cross-connector.

U.S. Pat. No. RE42,867 discloses an orthopedic device used to fix and stabilize bones to correct anomalies in skeletal structure occurring naturally or by trauma. Bone screws are screwed into bones by application of torque. Clamps are movably attached to the screws. Each clamp includes a compression ring. A connecting rod connects several screws through slots in the clamps. The clamps are tightened to hold the rod and the heads in a pre-selected position by linear movement of the compression rings.

U.S. Pat. No. 10,751,090 discloses a bone anchoring device having a receiving part with a recess for receiving a rod and a flexible head receiving portion for pivotably holding a head of a bone anchoring element, a pressure member configured to exert pressure on the head when the head is held in the head receiving portion, and a clamping ring positionable around the head receiving portion and movable from a first position where the head is pivotable relative to the receiving part, to a second position where the clamping ring exerts a radial force on the head receiving portion to lock the head relative to the receiving part. When the clamping ring is at the first position, the clamping ring abuts the receiving part to restrict upward movement, while a surface of the clamping ring that faces upwards is exposed for engaging an instrument to move the clamping ring to the second position.

U.S. Pat. No. 9,649,135 discloses a low profile orthopedic device using a clamp and compression ring to couple to a bone screw. The clamps are tightened to hold the rod to the bone screws in a preselected position by linear movement of the compression ring.

SUMMARY OF THE DISCLOSURE

The present system provides novel component devices and a method for selectively locking and unlocking a connector to a bone screw using an easily operated, torque-less locking and unlocking instrument specifically designed for use with the novel connector configuration. The spinal fixation system is for use in securing a spinal rod to a vertebra using a bone screw with a low profile lockable connector. The connector is configured to be movably connected to the head of a bone screw wherein a spinal rod can positioned to physically connect a first vertebra to a second vertebra. Once a bone screw has been attached, a connector on the bone screw can be locked in place allowing a spinal rod to be fitted. By locking of the connector to the bone screw, the connector can be used to move the vertebra along the spinal rod. The spinal fixation locking instrument includes a clamp for grasping a groove in the connector and an adjacent collet. The instrument is used to lock the connector to the bone screw by moving the collet from a first position to a second position. The connector can be selectively unlocked from the bone screw for adjustment or removal. Once the spinal rod and bone screw are placed into a desired position, the spinal rod is locked in position upon placement within the connector having a compression fit. In one embodiment the bone screw and connector are adjoined at the manufacturing stage. In another embodiment the bone screw and connector are modular allow bone screws of various shanks and sizes to be installed wherein the connector is bottom loading attached during the installation step.

An objective of the invention is to provide a spinal fixation system having a connector that is releasably lockable to a bone screw and providing for low profile rod coupling.

Another objective of the invention is to provide spinal fixation system having a connector operatively coupled to a lower collet having a first position which allows connector movement in relation to a bone screw and a second position which locks connector movement in relation to the bone screw.

Still another objective of the invention is to provide spinal fixation system having a connector operatively coupled to an upper collet having a first position which for receipt of a rod member in relation and a second position which locks the rod member to the connector.

Yet another objective of the invention is to provide a spinal fixation system that is preassembled or modular in installation.

An advantage of the system is that a surgeon can use the locking instrument to lock a connector to a bone screw. The surgeon can then place a stabilization rod within the connector for alignment purposes. The rod member can then be locked to the connector.

Another advantage is that the locked position of the connector to the screw provides great flexibility to the surgeon in making any adjustments deemed necessary such as, but not limited to, compression, distraction, and rotation of the entire construct or of individual bodies. After completing the adjustments, the surgeon can then fully lock the stabilization rod to the connector providing a low profile attachment.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

BRIEF DESCRIPTION OF THE DRAWINGS

FIG. 6A illustrates a top view of the bone screw with an unlocked connector;

FIG. 6B illustrates a cross-sectional side view taken along line AA of FIG. 6A;

FIG. 7A illustrates a top view of the bone screw locked to a connector;

FIG. 7B illustrates a cross-sectional side view taken along line AA of FIG. 7A;

FIG. 8A illustrates a top view of the bone screw with a locked connector having a rod inserted;

FIG. 8B illustrates a cross-sectional side view taken along line AA of FIG. 8A;

FIG. 9A illustrates a top view of the bone screw with a locked connector and locked rod;

FIG. 9B illustrates a cross-sectional side view taken along line AA of FIG. 9A;

DETAILED DESCRIPTION OF THE PREFERRED EMBODIMENTS

Figure 1A:
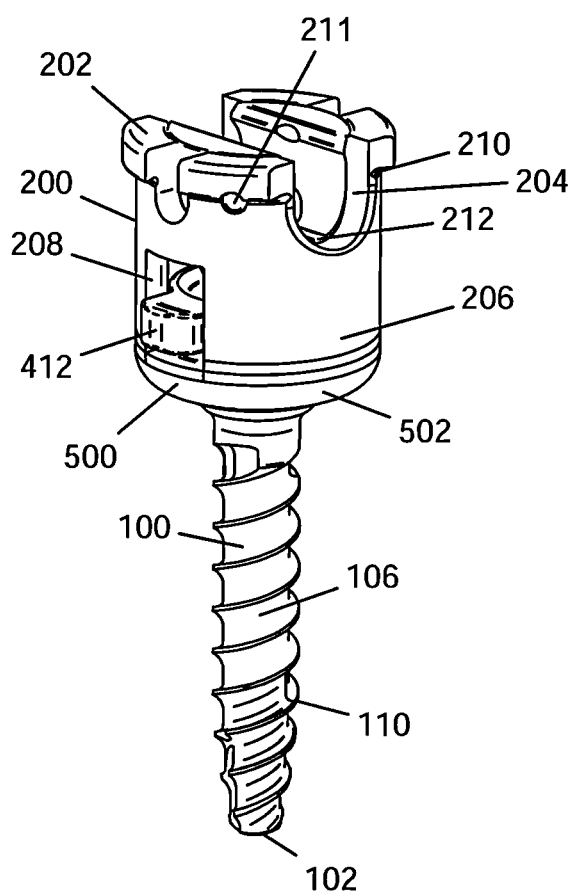
FIG. 1A illustrates an upper perspective view of the bone screw with lockable connector.
Figure 1B:
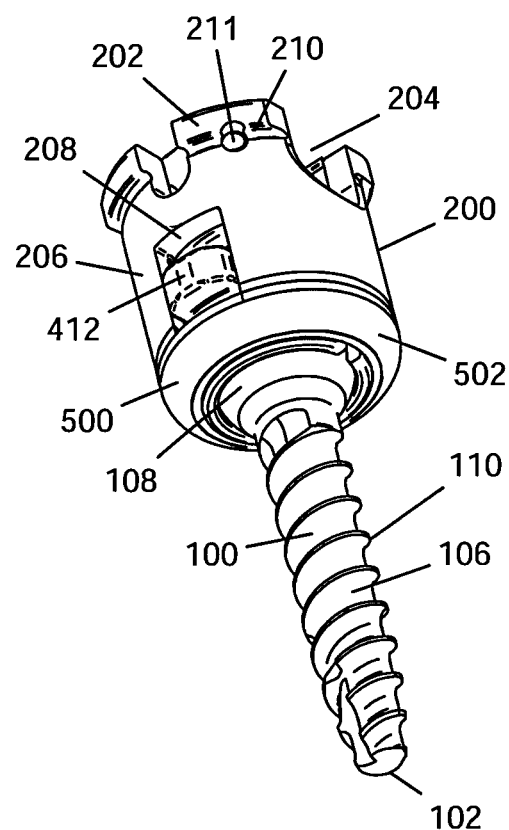
FIG. 1B illustrates a lower perspective view of FIG. 1A.
Figure 2A:
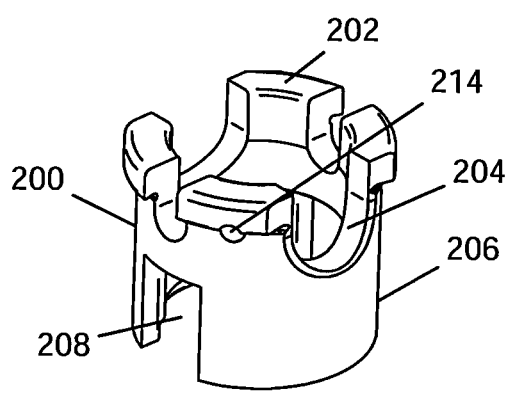
FIG. 2A illustrates a upper perspective view of the upper connector.
Figure 2B:
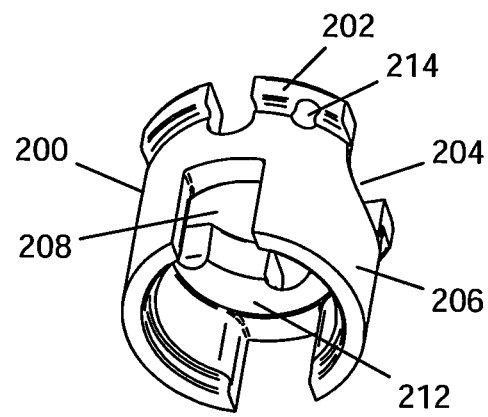
FIG. 2B illustrates a lower perspective view of FIG. 2A.
Figure 3A:
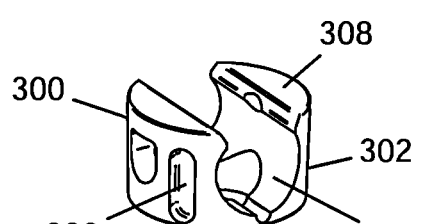
FIG. 3A illustrates an upper perspective view of the upper collet.
Figure 3B:
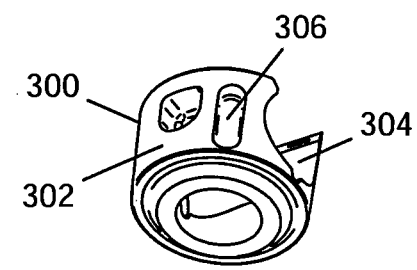
FIG. 3B illustrates a rear perspective view of FIG. 3A.
Figure 4A:
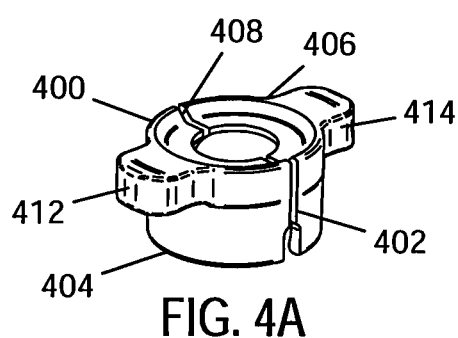
FIG. 4A illustrates an upper perspective view of the lower collet.
Figure 4B:
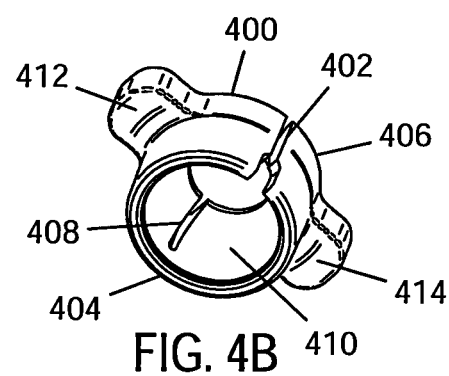
FIG. 4B illustrates a lower perspective view of FIG. 4A.
Figure 5A:
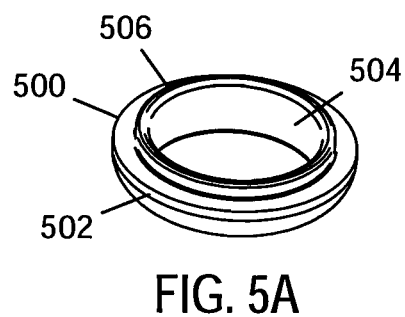
FIG. 5A illustrates an upper perspective view of the lower connector.
Figure 5B:
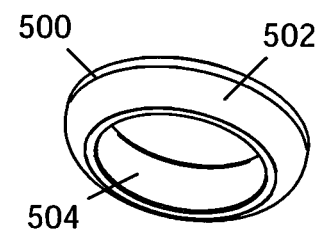
FIG. 5B illustrates a lower perspective view of FIG. 5A.
Figure 10:
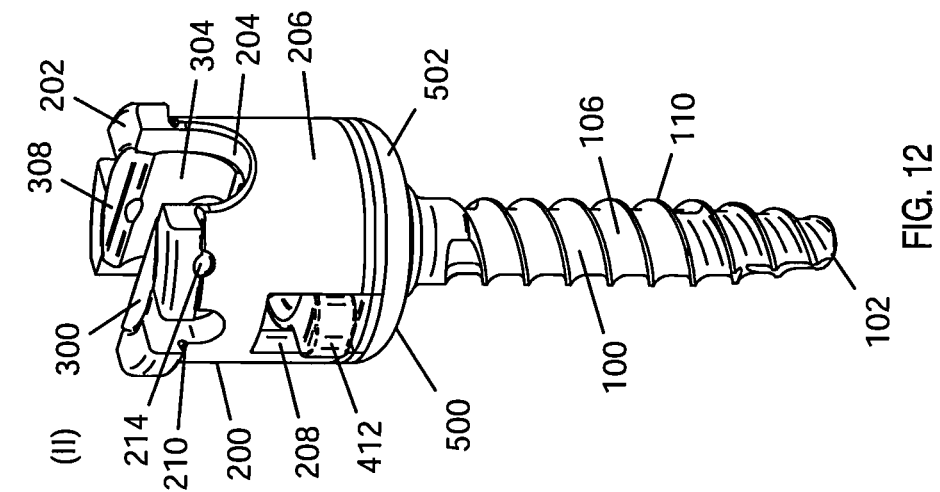
FIG. 10 is an upper perspective view of a connector unlocked to a bone screw.

Detailed embodiments are disclosed herein; however, it is understood that the following description is provided as being exemplary of the invention, which may be embodied in various forms without departing from the scope of the claimed invention. Thus, the specific structural and functional details provided in the description are non-limiting, but serve merely as a basis for the invention defined by the claims provided herewith.

Generally speaking, various embodiments of the present invention provide for a low profile spinal fixation device for orthopedic rod implantation. The invention is not limited to a specific size, diameter, or length and may accommodate a patient of any size, weight, and spinal condition. By way of example, the low profile spinal fixation device employs a pedicle screw that can vary in size, diameter, or length to accommodate the patient's needs. An advantage of the instant invention includes having a design that is able to lock the pedicle screw in place while maintaining a low profile so as to secure a spinal rod during a patient's orthopedic surgery.

Referring now to the Figures, illustrated is a preferred embodiment of the low profile spinal fixation device 10. The low profile spinal fixation device 10 includes a bone screw 100, also known as a "pedicle screw", having a first end 102 and a second end 104. Between the first end 102 and the second end 104 defines a shank portion 106 for penetrating securement to a bone. A surgeon will insert the bone screw 100 into the spine of a patient starting from the first end 102 and leading to the second end 104, which is constructed and arranged as a head portion 108. In a preferred embodiment, the head portion 108 is at least partially spherical in shape.

Further, the bone screw 100 includes at least one continuous thread 110 protruding outwardly from the shank 106 to engage with the bone and provide stabilization of the joint. In a preferred embodiment, the bone screw 100 includes at least one helical thread 110 for penetration and engagement of the bone. The size, shape, and pitch of the continuous thread 110 are not limiting. The pitch of the threads 110 may be consistent or variable. As illustrated in the Figures, continuous threads 110 that are consistent in pitch allow for a standardized size that is suitable as a spinal fusion surgery in most patients. Just as a traditional screw, the threads 110 decrease in diameter closer to the first end 102.

The low profile spinal fixation device 10 includes an upper connector 200 having an upper section 202 defining a first U-shaped channel 204 and a lower section 206 including a pair of spaced apart slots 208. In a preferred embodiment, the U-shaped channels 204 are further defined as two diametrically opposed openings. The upper connector 200 further includes an outer surface groove 210 formed perpendicular to the spaced apart slots 208. The groove 210 acts as a recess that allows a specialized tool to be inserted for the locking and unlocking operation of the low profile spinal fixation device 10. In between the upper section 202 and the lower section 206 exists an internal cavity 212 and a securement pin aperture 214. The securement pin aperture 214 is sized and shaped to receive a securement pin that limit movement of an upper collet 300 by engaging the elongated slot 306.

The upper collet 300 is sized and shaped to fit within the upper connector 200. The upper collet member 300 is formed from a substantially conical side wall 302 with a second U-shaped channel 304 in axial alignment with the first U-shaped channel 204 found on the upper connector 200. Each of the U-shaped channels 204, 304 are further defined as two diametrically opposed openings where a stabilizing rod 12 is positioned within the shaped openings. When the stabilizing rod 12 is secured by the upper collet 300, the upper collet 300 is compressed within the upper connector 200 for locking the stabilizing rod 12 in a fixed position. Further, the upper collet member 300 includes an elongated slot 306 operatively associated a securement pin 211 coupled to pin aperture 214 wherein the securement pin 211 protrudes into the elongated slot 306. The securement pin 211 regulates the movement of the upper collet 300 in relation to the length of the elongated slot 306.

The low profile spinal fixation device 10 includes a lower collet member 400 with a split 402 extending on one side from a lower edge 404 to an upper edge 406 and a partial split 408 extending on an opposite side extending adjacent to the lower edge 404 to the upper edge 406 forming a compression member. The total split 402 allows for the side wall of the lower collet member 400 to be press fit within a lower spherical seating surface 504 of a connector base 500. The lower edge 404 forms an upper spherical seating surface 410 for receipt of an upper portion of the bone screw spherical head 108. In a preferred embodiment, the seating surface 410 is sized and shaped to accommodate for the size and shape of the head portion 108 of the bone screw 100. The size and shape of the seating surface 410 is not limiting.

The lower collet member 400 includes a pair of tabs 412, 414 extending outwardly from the upper edge 406. The tabs 412, 414 fit directly and are slidably disposed within the spaced apart slots 208. This allows for the specialized tool to push medially downwards on the tabs 412, 414 of the lower collet member 400 to lock the bone screw 100 in place. The slidable engagement also allows the specialized tool to pull the lower collet member 400 laterally to unlock the bone screw 100 from the upper connector 200 as the tabs 412, 414 move laterally within the spaced apart slots 208. In particular, the low profile spinal fixation device 10 is specifically configured to be capable of releasably connecting to and operationally interacting with the upper connector 200 and the lower collet member 400 for moving the collet 400 from a first position (I) to a second position (II) within the slots 208, and from the second position (II) to the first position (I) for releasable engagement of the bone screw 100 to facilitate adjustment or removal of the stabilizing rod 12.

The low profile spinal fixation device 10 includes a connector base 500 having a continuous side wall 502 forming a lower spherical seating surface 504 for receipt of a lower portion of said bone screw spherical head 108. In an exemplary embodiment, the head portion 108 of the bone screw 100 fits directly into the lower spherical seating surface 504 by being similarly shaped and sized for a proper press fit connection. In an alternative embodiment, the lower spherical seating surface may be sloped and the lower collet member 400 is securable to the bone screw 100 by compression when moved along a sloped inner surface 504 of the lower connector 500. The connector base 500 itself is secured to the lower section 206 of the upper connector 200 securing the bone screw 100 and the collet 400 therebetween. In a preferred embodiment, the connector base 500 includes at least one ridge 506 securable to said lower section 206 of the connector 200 by weldment.

The low profile spinal fixation device 10 acts as a locking device specifically configured to be capable of releasably connecting to and operationally interacting with the upper connector 200 and the lower collet 400 for moving the lower collet 400 from a first position (I) to a second position (II) within the slots 208, and from the second position (II) to the first position (I) for releasable engagement of the connector 200 to the bone screw 100 to facilitate adjustment of the upper connector 200 to said bone screw 100.

Figure 11:
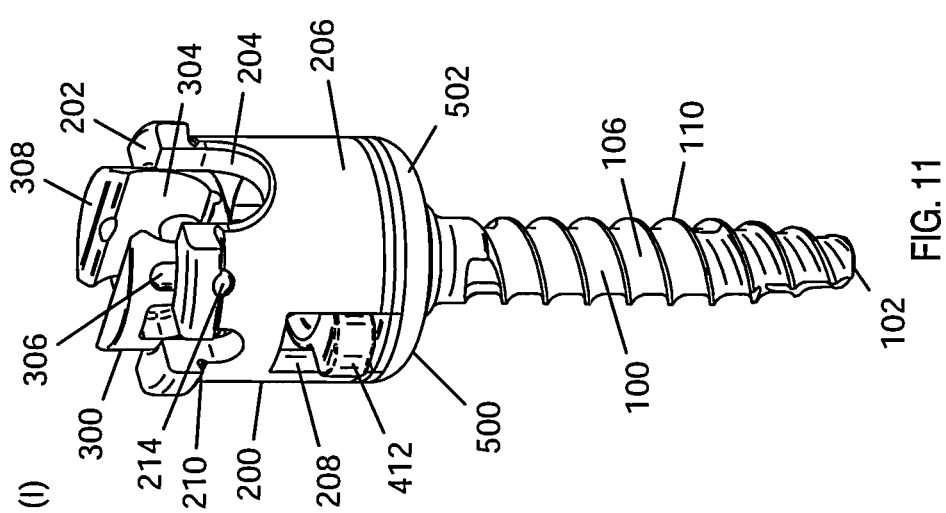
FIG. 11 is an upper perspective view of a connector locked to the bone screw.
Figure 12:
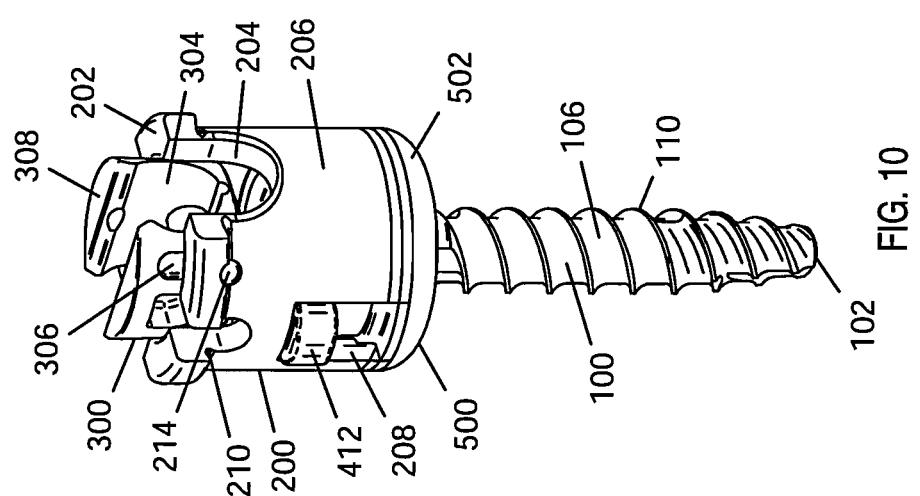
FIG. 12 is an upper perspective view of the upper collet in a locked position.

As illustrated in FIG. 6A to FIG. 12, the low profile spinal fixation device 10 can be fully locked when the upper collet member 300 and the stabilizing rod 12 are pushed fully downwards so that an upper edge 308 of the upper collet 300 is in line with the upper edge 202 of the upper connector 200, as specifically shown in FIGS. 8B and 9B. Further, the stabilizing rod 12 travels downwards until it contacts and engages the bottom surface of the U-shaped channels 204, 304 which further allows adequate clearance for the upper collet 300 to move from a locked position to an un-locked position. The lower collet 400 is movable from a first unlocked position (I) to a second locked position (II) for securing the upper connector 200 in a fixed position relative to the bone screw 100 whereby the upper collet 300 is movable from a first unlocked position (I) to a second locked position (II) for securing a stabilizing rod member 12 thereto, as shown in FIGS. 11 and 12.

The term "coupled" is defined as connected, although not necessarily directly, and not necessarily mechanically. The use of the word "a" or "an" when used in conjunction with the term "comprising" in the claims and/or the specification may mean "one," but it is also consistent with the meaning of "one or more" or "at least one." The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more: features. Furthermore, a device or structure that is configured in a certain way is configured in at least that way, but may also be configured in ways that are not listed.

One skilled in the art will readily appreciate that the present: invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred should be understood that the invention as embodiments, it not claimed should be unduly limited such specific embodiments. Indeed, various modifications of the described modes for carrying out the invention which are obvious to those skilled in the art are intended to be within the scope of the following claims.

What is claimed is:

1. A low profile spinal fixation device for orthopedic rod implantation, comprising:
   a bone screw having a first end and a second end, said first end constructed and arranged as a shank portion for penetrating securement to a bone, said second end constructed and arranged as a head portion;
   an upper connector having an upper section defining a first U-shaped opening and a lower section including a pair of spaced apart slots, said upper connector having an outer surface groove formed perpendicular to said slots, an aperture positioned between the upper and lower sections forming an internal cavity with a securement pin aperture positioned in said upper section;
   an upper collet member slidably insertable in said upper section of said upper connector formed from a substantially cylindrical side wall with a second U-shaped channel in axial alignment with a first U-shaped channel, and an elongated slot;
   a securement pin positioned in said pin aperture and protruding into said elongated slot, said securement pin regulating movement of said upper collet;
   a lower collet member slidably insertable into said lower section of said upper connector with a split extending on one side from a lower edge to an upper edge and a partial split extending on an opposite side extending adjacent to said lower edge to said upper edge forming a compression member, said lower edge forming an upper spherical seating surface for receipt of an upper portion of said bone screw spherical head portion, and a pair of tabs extending outward from the upper edge, said tabs slidably disposed within said spaced apart slots;
   a connector base having a continuous side wall forming a lower spherical seating surface for receipt of a lower portion of said bone screw spherical head portion, said connector base secured to said lower section of said upper connector securing said bone screw therebetween;
   wherein said lower collet member is movable from a first unlocked position to a second locked position for securing said upper connector in a fixed position relative to said bone screw whereby said upper collet is movable from a first unlocked position to a second locked position for securing a stabilizing rod member thereto.

2. The low profile spinal fixation device according to claim 1 wherein each said U-shaped channel is further defined as two diametrically opposed openings constructed and arranged to for receipt of the stabilizing rod member within the shaped openings.

3. The low profile spinal fixation device according to claim 2 wherein said upper collet is compressed within said upper connector for locking the stabilizing rod in a fixed position.

4. The low profile spinal fixation device according to claim 1 wherein said connector base includes at least one ridge securable to said lower section of said connector by weldment.

5. The low profile spinal fixation device according to claim 1 wherein said lower collet is securable to said bone screw by compression when moved along a sloped inner surface of said connector base.

6. The low profile spinal fixation device according to claim 1 wherein said bone screw includes at least one helical thread for penetrating and engaging a bone.

7. A low profile spinal fixation device for orthopedic rod implantation, comprising:
   a bone screw having a first end and a second end, said first end constructed and arranged as a shank portion for penetrating securement to a bone, said second end constructed and arranged as a partially spherical head portion;
   an upper connector having an upper section defining a first U-shaped opening formed from two diametrically opposed openings wherein a stabilizing rod is positioned within the shaped openings, and a lower section including a pair of spaced apart slots, said upper connector having an outer surface groove formed perpendicular to said slots, an aperture positioned between the upper and lower sections forming an internal cavity, with a securement pin aperture positioned in said upper section;

an upper collet member slidably insertable in said upper connector formed from a substantially cylindrical side wall with a second U-shaped channel in axial alignment with said first U-shaped channel, and an elongated slot;

a securement pin positioned in said pin aperture and protruding into said elongated slot, said securement pin regulating movement of said upper collet;

a lower collet member slidably insertable into said lower section of said upper connector with a split extending on one side from a lower edge to an upper edge and a partial split extending on an opposite side extending adjacent to said lower edge to said upper edge forming a compression member, said lower edge forming an upper spherical seating surface for receipt of an upper portion of said bone screw spherical head portion, and a pair of tabs extending outward from the upper edge, said tabs slidably disposed within said spaced apart slots;

a connector base having a continuous side wall forming a lower spherical seating surface for receipt of a lower portion of said bone screw spherical head portion, said connector base welded to said lower section of said upper connector securing said bone screw therebetween;

wherein said lower collet is movable from a first unlocked position to a second locked position for securing said upper connector in a fixed position relative to said bone screw whereby said upper collet is movable from a first unlocked position to a second locked position for securing a stabilizing rod member thereto.

8. The low profile spinal fixation device according to claim 7 wherein said upper collet is compressed within said upper connector for locking the stabilizing rod in a fixed position.

9. The low profile spinal fixation device according to claim 7 wherein said lower collet is securable to said bone screw by compression when moved along a sloped inner surface of said connector base.

10. The low profile spinal fixation device according to claim 7 wherein said bone screw includes at least one helical thread for penetrating and engaging a bone and wherein said head portion is at least partially spherical in shape.

* * * * *